(12) United States Patent
Garcia Saban et al.

(10) Patent No.: US 8,277,577 B2
(45) Date of Patent: Oct. 2, 2012

(54) METHOD FOR OBTAINING A SURFACE OF TITANIUM-BASED METAL IMPLANT TO BE INSERTED INTO BONE TISSUE

(76) Inventors: Francisco J. Garcia Saban, Barcelona (ES); Juan Carlos Garcia Saban, Barcelona (ES); Miguel Angel Garcia Saban, Barcelona (ES)

( * ) Notice: Subject to any disclaimer, the term of this patent is extended or adjusted under 35 U.S.C. 154(b) by 46 days.

(21) Appl. No.: 12/720,664

(22) Filed: Mar. 9, 2010

(65) Prior Publication Data

US 2010/0218854 A1    Sep. 2, 2010

Related U.S. Application Data

(63) Continuation of application No. PCT/ES2007/000555, filed on Oct. 3, 2007.

(30) Foreign Application Priority Data

Sep. 10, 2007  (ES) .................................. 200702414

(51) Int. Cl.
C23C 8/10      (2006.01)
A61F 2/02     (2006.01)
C03C 25/68   (2006.01)

(52) U.S. Cl. ........ 148/281; 148/240; 148/277; 148/284; 623/23.53; 623/23.55; 216/53; 216/83; 216/100; 216/108; 216/109; 451/75

(58) Field of Classification Search .................. 148/240, 148/277, 281, 284; 623/23.53, 23.55; 216/53, 216/83, 100, 108–109; 451/75
See application file for complete search history.

(56) References Cited

U.S. PATENT DOCUMENTS

| | | |
|---|---|---|
| 4,818,559 A | 4/1989 | Hama et al. |
| 5,603,338 A | 2/1997 | Beaty |
| 5,863,201 A | 1/1999 | Lazzara et al. |
| 5,876,453 A | 3/1999 | Beaty |
| 6,652,765 B1 | 11/2003 | Beaty |

(Continued)

FOREIGN PATENT DOCUMENTS

EP    1477141 A1    11/2004

(Continued)

OTHER PUBLICATIONS

C. Massaro, et al.,"Comparative investigation of the surface properties of commercial titanium dental implants, Part I: chemical composition", Journal of Materials Science: Materials in Medicine vol. 13, 2002, pp. 535-548.

(Continued)

*Primary Examiner* — Lois Zheng
(74) *Attorney, Agent, or Firm* — Myers Wolin, LLC

(57) ABSTRACT

The invention relates to a method for obtaining a surface of a titanium-based metal implant intended to be inserted into bone tissue, comprising: (a) projecting particles of aluminum oxide under pressure on the external area of the implant; (b) chemically treating the sandblasted external area of the implant with an acid composition comprising sulfuric acid and hydrofluoric acid; and (c) thermally treating the sandblasted external area of the implant by heating at a temperature of 200-450° C. for 15-120 min. The invention likewise defines a metal implant having said surface. The surface thus obtained has good micrometer-scale roughness with a suitable morphology, as well as a composition which is virtually free of impurities and a thickness which is approximately three times the thickness of conventional surfaces, which characteristics provide it with very good osseointegration properties.

10 Claims, 6 Drawing Sheets

U.S. PATENT DOCUMENTS

| | | | |
|---|---|---|---|
| 6,689,170 B1 | 2/2004 | Larsson et al. | |
| 2004/0167633 A1* | 8/2004 | Wen et al. | 623/23.57 |

FOREIGN PATENT DOCUMENTS

| | | | |
|---|---|---|---|
| EP | 1674051 | * | 6/2006 |
| EP | 2168527 A1 | | 3/2010 |
| ES | 2310129 | | 12/2008 |
| KR | 20030078480 | | 10/2003 |
| WO | 2004/008983 | | 1/2004 |

OTHER PUBLICATIONS

C. Sittig, et al., "Surface characterization of implant materials c.p. Ti, Ti—6Al—7Nb and Ti—6Al—4V with different pretreatments", Journal of Materials Science: Materials in Medicine, vol. 10, 1999, pp. 35-46.

International Search Report for corresponding International Application No. PCT/ES07/000555, mailing date of May 30, 2008.

International Preliminary Report on Patentablility for corresponding International Application No. PCT/ES07/000555, issued Dec. 18, 2009.

Buser, et al. "Influence of surface characteristics on bone integration of titanium implants. A histomorphometric study in miniature pigs", J. Biomedical Material Research, 25:889-902 (1991).

Wennerberg, et al. "Torque and histomorphometric evaluation of c.p. titanium screws blasted with 25 and 75-μm-sized particles of Al2O3", J. Biomedical Material Research, 30:251-260 (1996).

Buser et al. "Removal torque value of titanium implants in the maxilla of miniature pigs", Int. J Oral Maxillofacial Implants, 13:611-619 (1998).

Lazzara et al. "Bone response to dual acid-etched and machined titanium implant surfaces", Bone Engineering, Chap. 34 (2000).

Cochran et al. "Attachment and growth of periodontal cells on smooth and rough titanium", Int. J Oral Maxillofacial Implants, 9:289-297 (1994).

Martin et al. "Effect of titanium surface roughness on proliferation, differentiation, and protein synthesis of human osteoblast-like cells (MG63)", J Biomedical Material Research, 29:389-401 (1995).

Orsini et al. "Surface analysis of machined vs sandblasted and acid-etched titanium implants", Int. J. Oral Maxillofacial Implants, 15:779-784 (2000).

Sul, et al. "Oxidized implants and their influence on the bone response", J Material Science: Materials in Medicine, 12:1025-1031 (2001).

Palka, et al. "The effect of biological environment on the surface of titanium and plasma-sprayed layer of hydroxylapatite", Journal of Materials Science: Materials in Medicine, 9:369-373 (1998).

Gotfredsen, et al. "Anchorage of TiO2-blasted, HA-coated, and machined implants: an experimental study with rabbits"., J Biomedical Material Research, 29:1223-1231 (1995).

Franchi et al. "Early detachment of titanium particles from various different surfaces of endosseous dental implants", Biomaterials, 25: 2239-2246 (2004).

Guizzardi et al. "Different titanium surface treatment influences human mandibular osteoblast response", J Periodontol., 75:273-282 (2004).

Browne et al. "Characterization of titanium alloy implant surfaces with improved dissolution resistance", Journal of Materials Science: Materials in Medicine, 7:323-329 (1996).

Lee et al. "Surface characteristics of Ti6Al4V alloy: effect of materials, passivation and autoclaving", Journal of Materials Science: Materials in Medicine, 9:439-448 (1998).

Wieland et al. "Measurement and evaluation of the chemical composition and topography of titanium implant surfaces", Bone Engineering, Chap. 14 (2000).

* cited by examiner

METHOD FOR OBTAINING A SURFACE OF TITANIUM-BASED METAL IMPLANT TO BE INSERTED INTO BONE TISSUE

CROSS REFERENCE TO RELATED APPLICATIONS

This is a continuation under 35 U.S.C. 120 of International Application PCT/ES2007/000555 filed Oct. 3, 2007, which claims priority to Spanish Patent Application No. P200702414 filed Sep. 10, 2007, the contents of each of which are incorporated herein by reference.

FIELD OF THE INVENTION

The invention relates to the field of metal implants to be inserted into bone tissue. Specifically, the invention refers to a method for obtaining a metal implant surface that exhibits good roughness and has an optimised chemical composition and thickness resulting in a better cellular response, and therefore, a better implant-bone binding. The invention also refers to the metal implant that exhibits it.

BACKGROUND OF THE INVENTION

As is well known in the state of the art, some metals or metal alloys, such as titanium, zirconium, hafnium, tantalum, niobium, or alloys thereof, are used to form relatively strong links with bone tissue. In particular, metal implants of titanium and its alloys have been known since approximately 1950 for their properties of binding well to bone tissue. This binding was called osseointegration by Branemark et al. (Branemark et al., "Osseointegrated implants in the treatment of the edentulous jaw. Experience from a 10-year period", Scand. J. Plast. Reconstr. Surg., II, suppl 16 (1977)).

Although the binding between this metal and bone tissue is relatively strong, it is desirable to improve this binding. There are many methods developed in the state of the art to treat such metal implants to obtain a suitable surface on them to improve their osseointegration. The term "surface" is understood to refer to the superficial layer or most external zone of an implant, composed mainly of the oxide of the corresponding metal, the physical properties of which are clearly different from the massive material that the implant is made of.

Some of these methods are directed to altering the morphology of this superficial layer, increasing its roughness, in order to provide a higher area of contact, and therefore of binding, between the implant and the bone tissue, resulting in higher mechanical retention and strength, that is, in a better osseointegration of the implant.

The reason behind these procedures for increasing surface roughness are the studies carried out in the last few years (Buser et al., "Influence of surface characteristics on bone integration of titanium implants. A histomorphometric study in miniature pigs", J Biom Mater Res, (1991), 25:889-902; Wennerberg et al., "Torque and histomorphometric evaluation of c.p. titanium screws blasted with 25- and 75-um-sized particles of $Al_2O_3$", J Biom Mater Res, (1996); 30:251-260; Buser et al., "Removal torque value of titanium implants in the maxilla of miniature pigs", J Oral Maxillofac Implants (1998) 13:611-619; and Lazzara et al., "Bone response to dual acid-etched and machined titanium implant surfaces", Bone Engineering, chap. 34 (2000) J. E. Davies eds.), which demonstrate that osseointegration of the implant in the short and medium term is improved by a micrometric surface roughness.

Also, other studies (Buser et al. 1991, supra; Cochran et al., "Attachment and growth of periodontal cells on smooth and rough titanium", Int. J Oral Maxillofac Implants (1994) 9:289-297; Martin et al., "Effect of titanium surface roughness on proliferation, differentiation, and protein synthesis of human osteoblast-like cells (MG63)", J Biom Mat Res (1995) 29:389-401; Lazzara et al. 2000, supra; and Orsini et al., "Surface analysis of machined vs sandblasted and acid-etched titanium implants", J. Oral Maxillofac Implants (2000) 15:779-784) have demonstrated that the existence of a superficial layer on the implant of a micrometric roughness improves osteoblast cellular expression, giving rise to better cellular differentiation and better osteoblast expression. The consequence of this effect is an improved osseointegration and a more bone formation.

Also, some more research-based manufacturers, such as Nobel Biocare, have designed such surface treatments so that they increase the thickness and the crystallinity of the titanium oxide layer, as some studies seem to suggest a relationship between the degree of crystallinity and better osseointegration of the implant (Sul et al., "Oxidized implants and their influence on the bone response", J Mater Sci: Mater in Medicine (2002); 12:1025-1031).

The methods used in the state of the art to increase surface roughness of an implant are very diverse. Among them can be highlighted the application of a coating over the surface, blasting of the surface with particles and chemical attack of the surface.

The common methods of coating the metal implant surface consist in applying a metal coating, normally of titanium, or a ceramic layer, normally of hydroxyapatite, by various known techniques such as plasma pulverisation or plasma spray (Palka, V. et al., "The effect of biological environment on the surface of titanium and plasma-sprayed layer of hydroxylapatite". Journal of Materials Science: Materials in Medicine (1998) 9, 369-373).

In the case of blasting the surface, particles of various materials and sizes are used, which are blasted on the surface of the implant in such as way as to alter its morphology. Usually, particles of corundum (alumina) are used (Buser et al. 1991, supra; Wennerberg et al. 1996; supra), or particles of titanium oxide (Gotfredsen, K. et al., "Anchorage of TiO2-blasted, HA-coated, and machined implants: an experimental study with rabbits". J Biomed Mater Res (1995) 29, 1223-1231).

On the other hand, chemical attack of the surface is carried out using various mineral acids such as hydrofluoric acid, hydrochloric acid, sulfuric acid, etc. So, for example, in a series of United States patents by Implant Innovations Inc. (U.S. Pat. No. 5,603,338; U.S. Pat. No. 5,876,453; U.S. Pat. No. 5,863,201 and U.S. Pat. No. 6,652,765) a two-stage acid treatment is described that is used to obtain the commercial Osseotite® surface. In the first stage, aqueous hydrofluoric acid is used to remove the natural oxide layer on the metal surface; in the second stage a mixture of hydrochloric acid and sulfuric acid is used to obtain a micrometric rough surface. In the European patent application EP 1477 141, also from Implant Innovations Inc., a variation of this method is described in which a mixture of hydrofluoric acid and hydrochloric acid is used in the second stage to treat implant surfaces based on titanium and Ti6Al4V alloys.

The combined use of both techniques has also been described, that is, blasting of the implant surface followed by chemical attack. So, Buser (Buser et al. 1991, Buser at al. 1998, supra) described, among other methods, blasting with medium grain alumina followed by etching with a mixture of hydrofluoric and nitric acids; also blasting with coarse alumina followed by chemical treatment with a mixture of hydrochloric and sulfuric acids. Similarly, Cochran (Cochran et al. 1994, supra) used blasting with fine or coarse corundum particles followed by a chemical treatment with hydrochloric and sulfuric acids to treat a titanium surface. Similarly, Choi Seok et al. (KR 2003007840) described blasting with calcium phosphate particles followed by treatment with a mixture of hydrochloric and sulfuric acids. Equally, in the document WO 2004/008983 by Astra Tech, a method of treatment of implant surfaces was described that combined blasting with fine and coarse particles of titanium oxide followed by treatment with hydrofluoric acid. Also, Franchi (Franchi et al., (2004) "Early detachment of titanium particles from various different surfaces of endosseous dental implants", Biomaterials 25, 2239-2246) and Guizzardi (Guizzardi et al., (2004) "Different titanium surface treatment influences human mandibular osteoblast response", J Periodontol 75, 273-282) described blasting with fine and coarse zirconia particles followed by an unspecified acid treatment.

Regarding thermal treatment, Browne (Browne et al. (1996), "Characterization of titanium alloy implant surfaces with improved dissolution resistance", Journal of Materials Science: Materials in Medicine 7, 323-329) and Lee (Lee et al. (1998), "Surface characteristics of Ti6Al4V alloy: effect of materials, passivation and autoclaving", Journal of Materials Science Materials in Medicine 9, 439-448) described the treatment of a previously untreated titanium alloy with hot air at 400° C. for 45 minutes to achieve better resistance to dissolution and a higher thickness of the oxide layer; although the thickness achieved was only 4 nm.

By means of these methods, therefore, surfaces with micrometric roughness are obtained but with a very much reduced surface titanium oxide thickness, which entail the disadvantages of not having a very stable titanium oxide layer and not reducing the release of metal ions to the medium.

The state of the art, therefore, continues to require alternative methods of treating the superficial layer of metal implants that provide a micrometric surface roughness and with improved chemical composition and thickness in order to optimise the process of their osseointegration.

Spanish patent application 200701518 of the present authors describes a method for obtaining a surface of titanium-based metal implants which is virtually free from impurities, with a thickness which is approximately three times the thickness of conventional surfaces, and with a micrometer-scale roughness and morphology (FIGS. 1a and 2a) optimizing the osseointegration and bone anchorage processes.

Said method consists of projecting particles of zirconium oxide under pressure to sandblast the external area of the implants, followed by a subsequent chemical treatment with a particular combination of acids and by a final thermal treatment. The use of a mixture of sulfuric acid and hydrofluoric acid, as well as the combination of these three treatment and the conditions of the final thermal treatment had not been described until then.

The present inventors have now found that in the sandblasting process of the previous method, the substitution of the type of particles together with the modification of their size and the pressure at which they are projected allows obtaining an alternative surface of a metal implant with a micrometer-scale morphology which is different but also suitable for optimizing the osseointegration and bone anchorage processes.

Therefore, the method of the present invention allows obtaining alternative surfaces of titanium-based metal implants with optimized properties in relation to chemical composition, thickness, and micrometer-scale roughness and morphology which translate into good osseointegration and cell response properties.

OBJECT OF THE INVENTION

The object of the present invention is, therefore, to provide a method for obtaining a surface of a titanium-based metal implant intended to be inserted into bone tissue.

Another object of the invention is to provide the surface obtainable by said method.

Finally, another object of the invention is to provide a metal implant that exhibits said surface.

DETAILED DESCRIPTION OF THE INVENTION

Figure 1A:
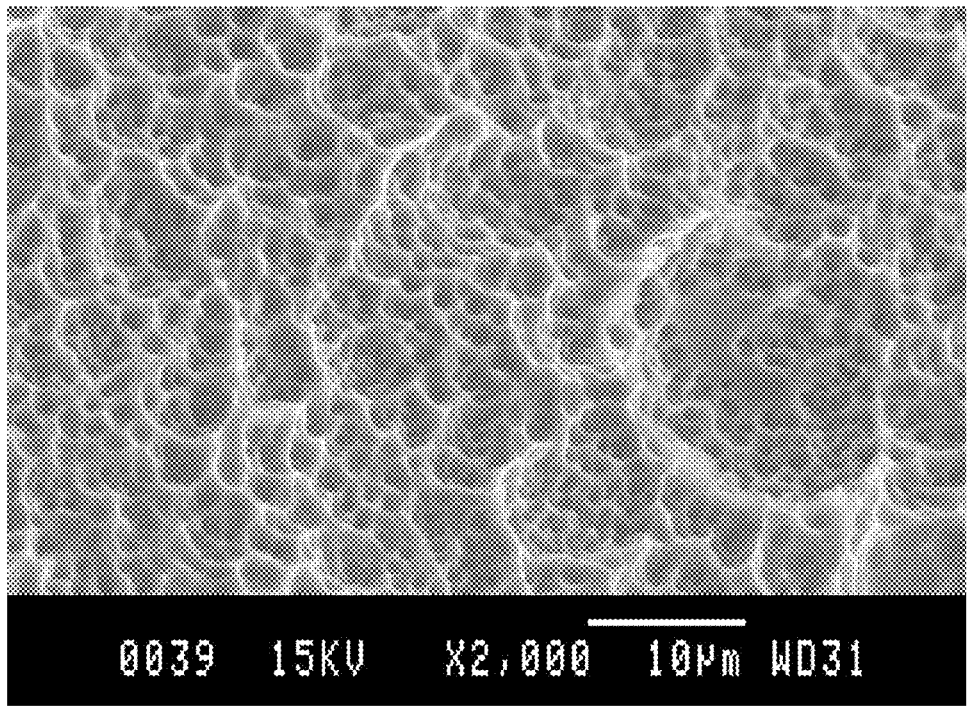
FIG. 1a shows a micrograph (150×) of the surface obtained by the previous method of the present inventors.

The present invention provides a method for obtaining a surface of a titanium-based metal implant intended to be inserted into bone tissue, hereinafter "method of the invention", comprising the steps of:

(a) projecting particles of aluminium oxide under pressure on the external area of the implant;

(b) chemically treating the sandblasted external area of the implant with an acid composition comprising sulfuric acid and hydrofluoric acid; and (c) thermally treating the sandblasted and chemically treated external area of the implant by heating at a temperature of 200-450° C. for 15-120 min.

As indicated above, the surface of a titanium-based implant is the superficial layer or outermost area thereof composed mainly by titanium oxide.

The surface obtained by the method of the invention has a thickness of 8-50 nm, particularly of 10-30 nm and more particularly of 15 nm. Said thickness, which is almost three times the thickness of conventional surfaces, involves a greater osseointegration of the implant, in addition a considerable reduction of the impurities, as has been previously indicated.

Likewise, the surface obtained by the method of the invention comprises an almost stoichiometric composition of titanium oxide, of approximately 98% by weight. (percentage measured by means of XPS, or photoemission spectroscopy, after 1 minute of sputtering, or bombardment with accelerated ions, to eliminate the contamination present in the external area of the surface obtained, which is inherent to the analysis method, and obtain the actual composition thereof).

The surface obtained by the method of the invention additionally has good micrometer-scale roughness and, therefore, very good osseointegration and cell response properties. In fact, the morphology of the treated surface is similar to the trabecular bone, optimized for the start of the bone repair. Likewise, its porosity and roughness characteristics allow the homogenization of residual stresses, the adhesion and fixing of the initial proteins, as well as cell adhesion, proliferation and maturation and the stability of extracellular matrix.

The metal implant to be treated is a titanium or titanium alloy implant. The titanium can be commercially pure titanium, for example. Likewise, the titanium alloy can be any suitable titanium alloy such as the titanium, aluminium and vanadium alloy Ti6Al4V, for example. Said titanium-based metal implant is suitable for being inserted into bone tissue, therefore it can be a dental implant, orthopedic implant, etc., depending on the bone tissue into which it is intended to be inserted.

In a particular embodiment of said method, the projection of the particles of aluminium oxide on the external area of the implant of step (a) is performed at a pressure of 1-6 atm. In a preferred embodiment, the projection of the particles of aluminium oxide is performed at a pressure of 3 atm.

In another particular embodiment of the method of the invention, the particles of aluminium oxide used in step (a) have a particle size of 10-100 μm. In a preferred embodiment, said particles of aluminium oxide have a particle size of 25 μm.

Upon sandblasting with particles of aluminium oxide, biocompatibility problems are prevented from occurring in the event that there are remains of such particles at the end of the process, since it is a very biocompatible material. Furthermore, the particles of this material and size have numerous sharp arises and edges, which, combined with the pressure of the sandblasting, cause a point of impact with a pronounced concave shape, suitable for the good cell response.

Any suitable device, such as Renfert brand Basic Quattro model sandblasting equipment can be used to perform the sandblasting, or homogenization of machining stresses. Said equipment is connected to a pressurized air circuit, which projects the aluminium oxide grit with which the machine is loaded. Once the sandblasting is over, the surface is cleaned by any suitable method of the art, such as by applying pressurized air and subsequent ultrasound cleaning treatment.

In a particular embodiment of the method of the invention, the acid composition used in step (b) comprises 15-50% (v/v) sulfuric acid and 0.01-1% (v/v) hydrofluoric acid. In a preferred embodiment, said acid composition comprises 28.8% (v/v) sulfuric acid and 0.024% (v/v) hydrofluoric acid.

This particular combination of acids produces a particular roughness and morphology which, combined with the surface chemical composition obtained with hardly any impurities, cause an optimal cell response.

In another particular embodiment of the method of the invention, the chemical treatment of step (b) is performed at a temperature of 50-110° C. for 4-60 min. In a preferred embodiment, said chemical treatment is performed at a temperature of 75° C. for 12 min.

Standard laboratory implements are used for the etching, inside a fume hood (Cruma brand 9001-GH model air hood, for example) to prevent acid vapors. After the chemical treatment, the implant is removed from the acid bath, washed to remove the remaining acid and subsequently cleaned by means of ultrasound and dried. For the drying, a suitable conventional drying device can be used, such as a Renfert brand drying oven.

In another particular embodiment of the method of the invention, the thermal treatment of step (c) is performed at a temperature of 285° C. for 60 minutes.

This thermal treatment at the indicated temperature and for the stipulated time causes a restructuring of the surface titanium oxide layer, with an increase of the crystallinity and a reduction of the impurities, which entails an improvement of the cell response. Furthermore, said thermal treatment increases the thickness of the surface titanium oxide layer. Under normal conditions, titanium exposed to the atmosphere oxidizes and generates a titanium oxide layer with a thickness of about 5 nanometers. This oxide layer protects the rest of the titanium from oxidizing. It is thus interesting to obtain a titanium oxide layer with increased thickness, but not so much that the fragility of said layer can cause the generation of microparticles upon rubbing with the bone while inserting the implant. The range of thickness obtained by the method of the invention of 8 to 50 nm is acceptable in this sense.

Thus, to obtain the mentioned thickness, the thermal treatment must be performed at a temperature sufficient to accelerate the diffusion of atmospheric oxygen in the material, and not high enough to cause an oxidation in the titanium that will be visible by a change in the colour. The working temperature selected therefore varies between 200° C. and 450° C.

Finally, the treatment time is the second parameter which must be controlled. A very reduced time does now allow the effective diffusion of oxygen. A time that is too long causes excessive increases in the thickness of the layer and cannot be industrialized. A reasonable range between these two extremes would be located between 15 minutes and 24 hours, depending on the treatment temperature. The working time selected therefore varies between 15 and 120 minutes.

This thermal treatment is performed by conventional means, using a low-temperature Memmert UM-100 model oven, for example.

In another aspect of the invention, a surface obtainable by the previously described method is provided. As has been indicated, said surface comprises substantially pure titanium oxide and has a thickness of 8-50 nm, particularly of 10-30 nm and more particularly of 15 nm.

In another aspect of the invention, a titanium-based metal implant intended to be inserted into bone tissue, having the surface obtainable by the previously described method, is provided. In a particular embodiment, said metal implant is a titanium or titanium alloy implant. In another particular embodiment, said metal implant is a dental implant.

The following examples illustrate the invention and must not be considered as limiting the scope thereof.

Example 1

Obtaining a Titanium Dental Implant with a Surface Obtainable by the Method of the Invention A Defcon TSA threaded cylindro-conical endosseous implant made of commercially pure titanium was subjected to a projection of 25 μm particles of aluminium oxide under a pressure of 3 atm, placing the exit nozzle perpendicular to the surface to be treated, at a distance of between 2 and 3 cm.

After the sandblasting, it was cleaned with pressurized air and subsequently submersed in pure water in ultrasound for 10 minutes. It was then dried by means of compressed air.

An aqueous solution was then prepared with the following composition: 28.8% by volume of sulfuric acid and 0.024% by volume of hydrofluoric acid. The beaker with the reagent was placed in a thermal bath, setting the temperature to be reached by the reagent to 75°+/−2° C. Once the desired temperature of the reagent was reached, the chemical treatment was performed by means of immersing the previously sandblasted implant in the reagent solution for 12 minutes (+/−15 seconds). Once said treatment ended, the implant was removed from the acid bath and diluted by means of shaking for about 15 seconds in two pure water baths consecutively. It was then submersed in pure water in ultrasound for about 10 minutes and subsequently dried in an oven.

Finally, the thus treated implant was subjected to a final thermal treatment at a temperature of 285° C. (+/−20° C.) for 60 minutes in a low-temperature Memmert UM-100 model oven.

Example 2

Characterization of the Surface Obtained in Example 1

Morphology

The morphology of the surface obtained in Example 1 was studied by means of surface micrographs and measurement of the roughness by confocal microscopy.

Surface Micrographs

The surface micrographs were carried out in a JEOL JSM 840 scanning electron microscope, with a scanning beam potential of 15 kV.

Figure 1B:
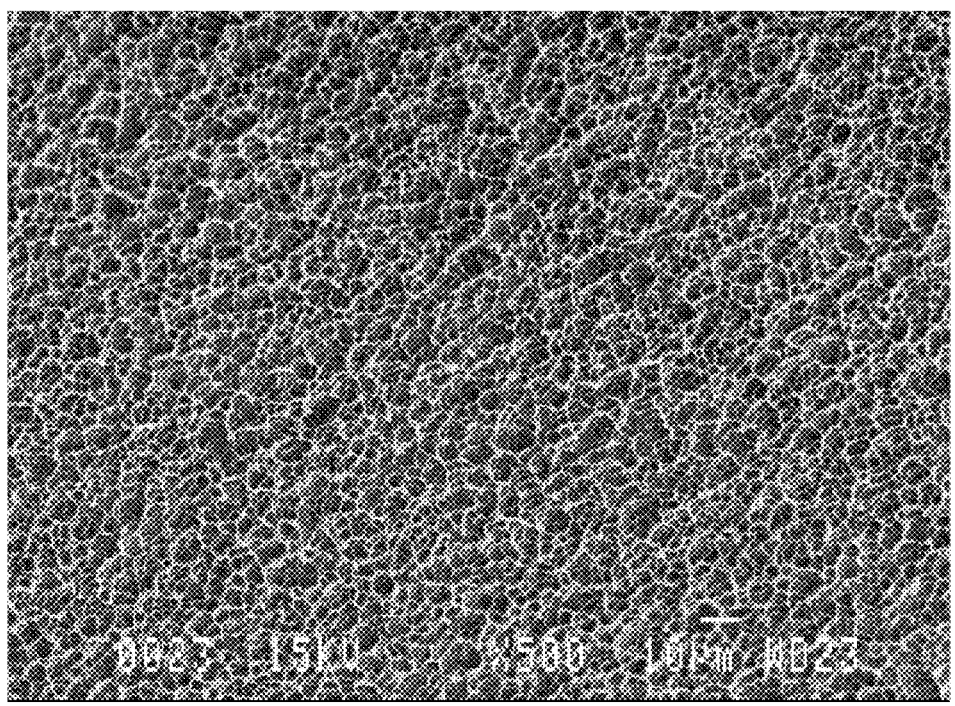
FIG. 1b shows a micrograph (150×) of the surface obtained by the method of the invention.

FIG. 1b shows a (150×) micrograph of said surface in which it is seen that the surface has very characteristic surface roughness, with values of roughness $R_a$ (average roughness) of about 1 μm, characterized by a rounded morphology with sharp outer edges and the presence of a homogeneously distributed deep porosity, due to the action of the acid etching on the surface.

This level of roughness allows complying with the requirements indicated by various scientific articles (Buser et al. 1991, Cochran et al. 1994, Martin et al. 1995, Wennerberg et al. 1996, Wennerberg et al. 1997, Buser et al. 1998, Lazzara et al. 2000, Orsini et al. 2000, supra) in relation to the need of having on the surface of the implant a roughness allowing a good anchorage of the cells.

Measurement of the Roughness by Confocal Microscopy

The measurement of roughness in 3D was performed with a confocal microscope connected to the software PLμ, developed by the Optics Department of the Escuela Técnica Universitaria de Terrassa (Universitat Politècnica de Catalunya). The measurements were made according to the DIN 4768 standard, with an 800 μm cut-off Gaussian filter.

Figure 2A:
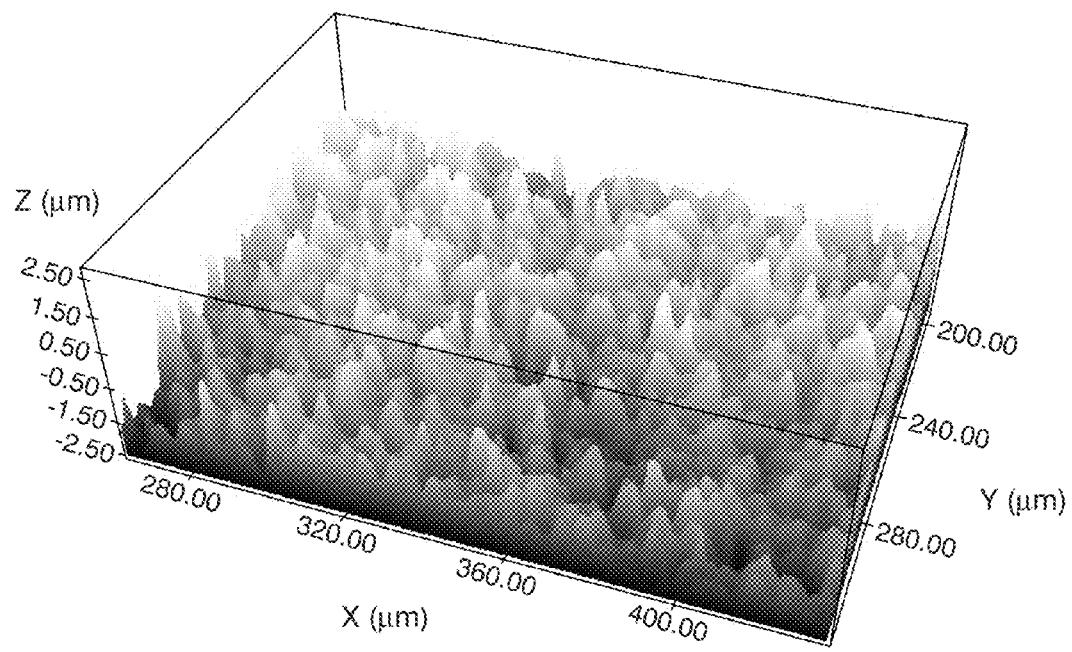
FIG. 2a shows the roughness in three dimensions obtained by confocal microscopy of the surface obtained by the previous method of the present inventors.
Figure 2B:
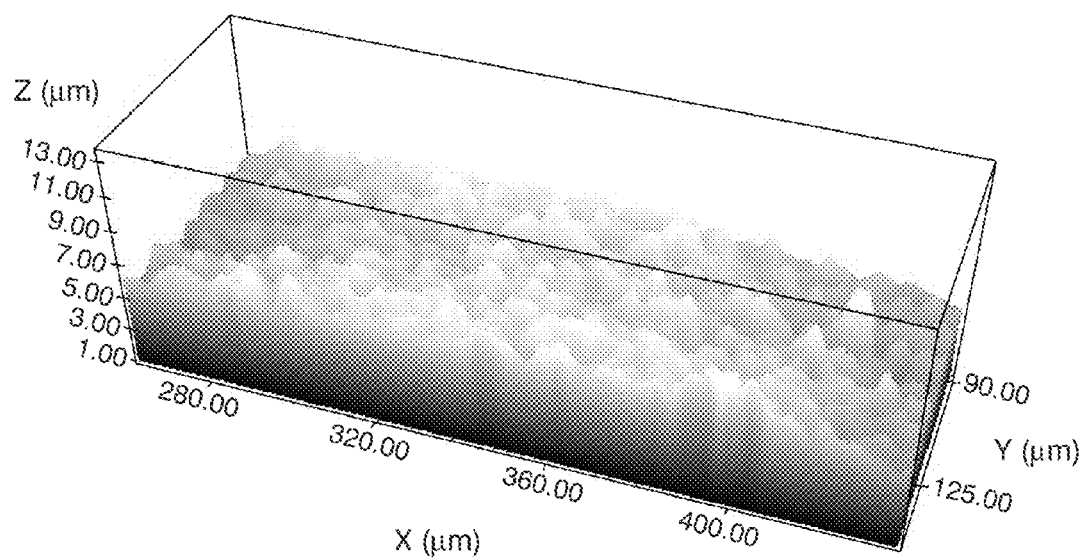
FIG. 2b shows the roughness in three dimensions obtained by confocal microscopy of the surface obtained by the method of the invention.
Figure 3:
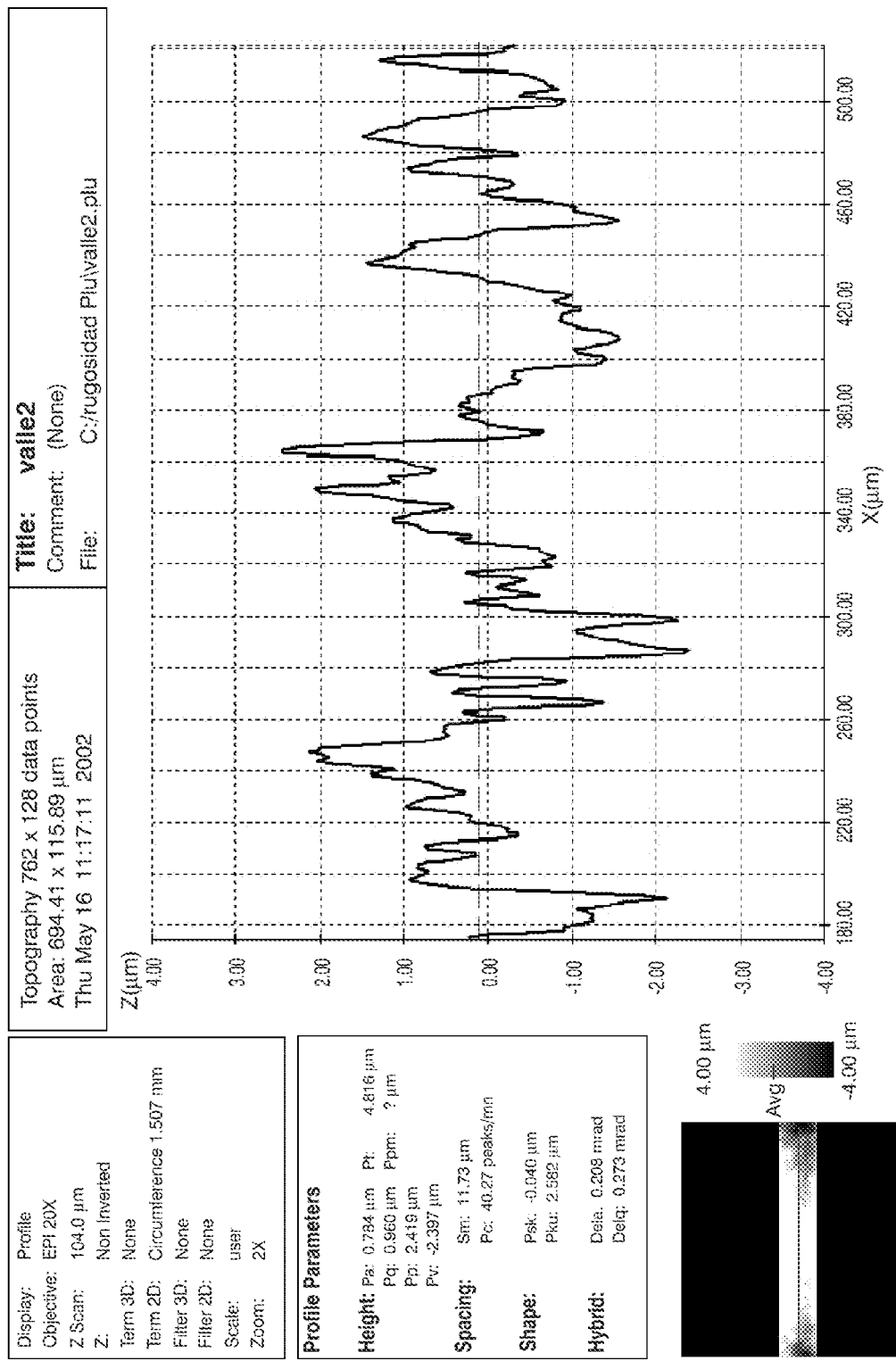
FIG. 3 shows the reconstruction of the sector of an outer thread area of the implant and the measurement of the corresponding roughness of the surface obtained by the method of the invention.

FIG. 2b shows the roughness in three dimensions of the surface obtained by means of this technique. Likewise, FIG. 3 shows the reconstruction of the sector of an outer thread area of the implant and the measurement of the corresponding roughness according to a transverse profile of the surface.

The values of roughness obtained give average values of $R_a$ (average roughness) of 1.0 μm, with a spacing between peaks $S_m$ of 12 μm. These values are close to the values mentioned as desirable in the literature referred to in the previous section.

Surface Chemical Composition

The analysis of the surface chemical composition was performed by means of two different techniques: analysis by energy-dispersive X-rays (EDS), and analysis by photoelectron spectrometry (XPS).

Analysis by Energy-Dispersive X-rays (EDS)

This technique allows determining the quantitative composition of a surface in a thickness of approximately 1 μm with a high spatial resolution. EDS allows detecting the presence of atoms with an atomic weight comprised between boron and uranium, and quantifying their presence in the studied surface.

Figure 4:
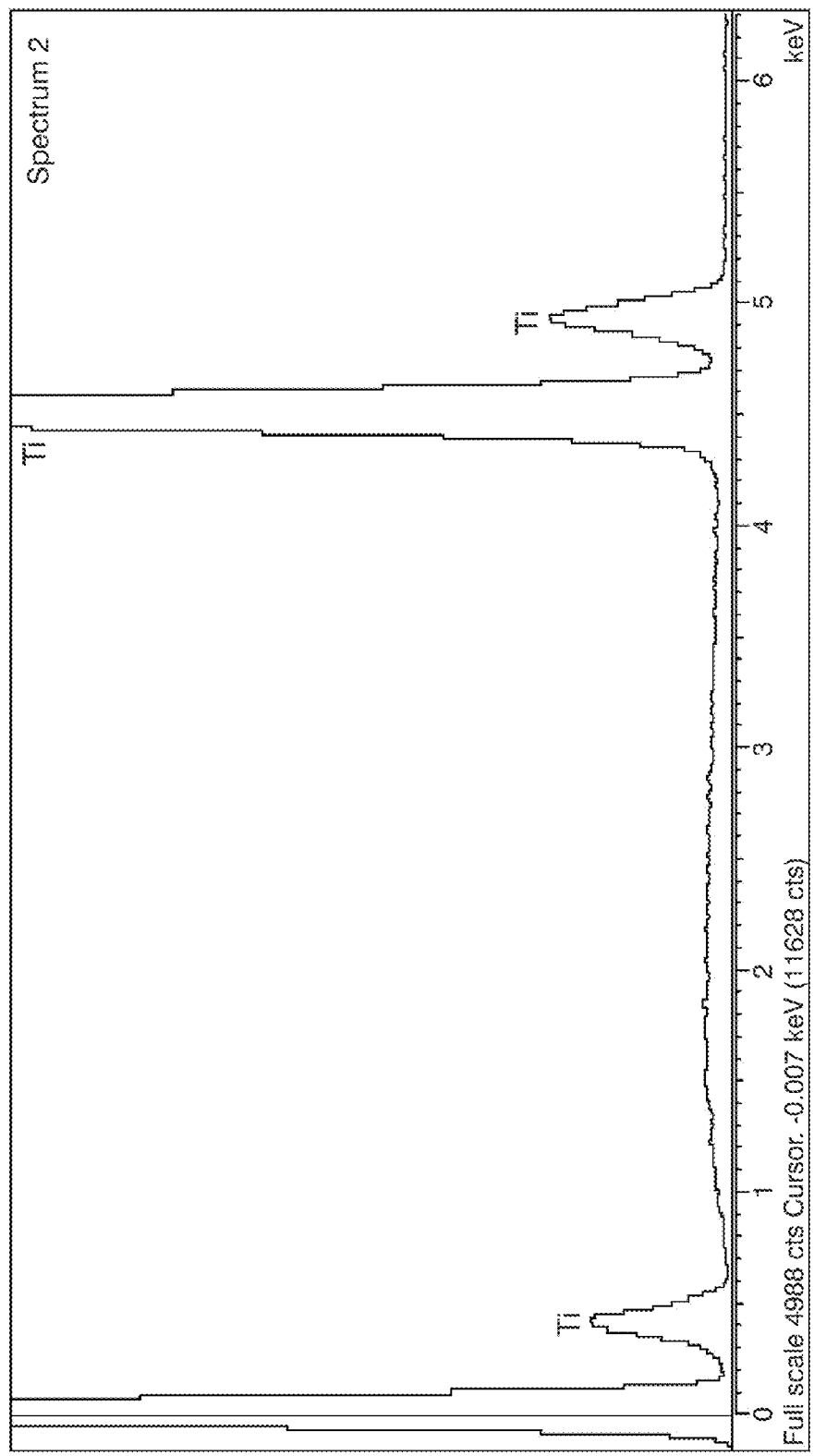
FIG. 4 shows the energy-dispersive X-ray spectrum (EDS) of the surface obtained by the method of the invention.

The EDS measurements were made in the Scientific-Technical Services of the Universitat de Barcelona. A Leica Electroscan 360 SEM, with EDS Link-Inca equipment capable of detecting atoms with an atomic weight equal to or greater than that of boron, was used to that end. FIG. 4 shows the energy-dispersive X-ray spectrum (EDS) obtained.

The analyses performed by means of EDS have only shown the presence of titanium and of oxygen in the surface of the titanium sample treated, with an occasional trace of aluminium. The presence of aluminium is due to the effects of the previous stress homogenization treatment, which can leave some particles of aluminium oxide adhered in the surface. The different analyses show that this behavior occurs in the entire surface of the treated implant.

Analysis by Photoemission Spectrometry (XPS)

The XPS analyses were performed by the ESCA and TEM Analysis Unit of the Scientific-Technical Services of the Universitat de Barcelona. The results (in atomic percentages) are shown in Table 1, together with a comparison with XPS analyses mentioned in the literature of several dental implants (Wieland et al., "Measurement and evaluation of the chemical composition and topography of titanium implant surfaces", *Bone Engineering*, chap. 14 (2000) J. E. Davies eds; Massaro et al., "Comparative investigation of the surface properties of commercial titanium dental implants. Part I: chemical composition". *J Mat Sci: Mat in Medicine* (2002) 13: 536-548).

TABLE 1

Results of the analysis of the surface of the samples performed with XPS, compared with those of the surface of other commercial implants.

| | C (%) | O (%) | Si (%) | N (%) | Ti (%) | Na (%) | Cl (%) | TiO$_2$ Layer (nm) |
|---|---|---|---|---|---|---|---|---|
| Surface[1] | 46.0 | 38.2 | — | 2.0 | 13.8 | — | — | 15 |
| Sputtering 1 minute[2] | 5.1 | 54.0 | — | 0.4 | 38.2 | — | — | 15 |
| Machined Brånemark[3] | 29.8 | 51.9 | — | — | 12.8 | 5.0 | 0.5 | 5.7 |
| ITI SLA[4] | 34.9 | 51.4 | traces | 1.3 | 14.5 | — | — | 5.7 |
| 3i Osseotite[5] | 53.7 | 36.2 | 3.3 | 5.4 | 6.8 | traces | traces | N.a. |

[1]Surface of the invention analyzed without "sputtering" (includes the detection of the contamination present in the outermost area of the surface obtained and which is inherent to the analysis method).
[2]Surface of the invention after 1 minute of sputtering.
[3]Machined Brånemark: without treatment, only mechanical process (Nobel Biocare).
[4]ITI SLA: sandblasting + acid treatment (Straumann).
[5]3i Osseotite: acid treatment (Biomet 3i).
N.a.: Not available.

The comparison of results shows that the chemical composition of the surface of the samples analyzed is perfectly equivalent to that of other implants present on the market, even with a lower presence of carbon or silicon impurities (Wennerberg et al. 1996, supra; Wieland et al. 2000, supra; and Sittig et al., "Surface characterization of implant materials c.p. Ti, Ti6Al7Nb and Ti6Al4V with different pretreatments", *J Mater Sci: Mater in Medicine* (1999), 10:35-46).

The presence of some elements in the surface, such as nitrogen, is due to the thermal treatment process. The presence of other contaminants common in other processes, such as silicon or sodium has not been detected. The residual % up to 100% is due to the argon detected (not indicated), which is a residue of the XPS measurement process.

Example 3

Cell Response of the Surface of a Titanium Sample Obtained by a Method Similar to that Described in Example 1

A study was conducted by the 063-13 research group (Pharmacology Department, School of Medicine and Odontology, Univ. Santiago de Compostela, Spain) for the biological evaluation of titanium samples (commercial pure titanium discs with a diameter of 5 mm) treated by means of a method similar to that described in Example 1.

Human osteoblasts were seeded in work samples ($8 \times 10^3$ cells/disc in triplicate) in modified Dulbecco culture medium, with 10% fetal bovine serum and 1% antibiotic solution. Cell bioactivity (indicator of the cytotoxicity of the surface) and alkaline phosphatase production (indicator of bone matrix production by the osteoblasts) of the surface obtained by the method of the invention (code 03/136-14) were measured with respect to those of an untreated surface of the same titanium machined (code 03/136-07), another untreated surface of the same titanium subjected to sandblasting (polished with silicon carbide polishing paper of about 5 micrometers) (code 03/136-18) and an untreated surface subjected to sandblasting plus acid treatment similar to the ITI SLA surface (code 03/136-09).

Figure 5:
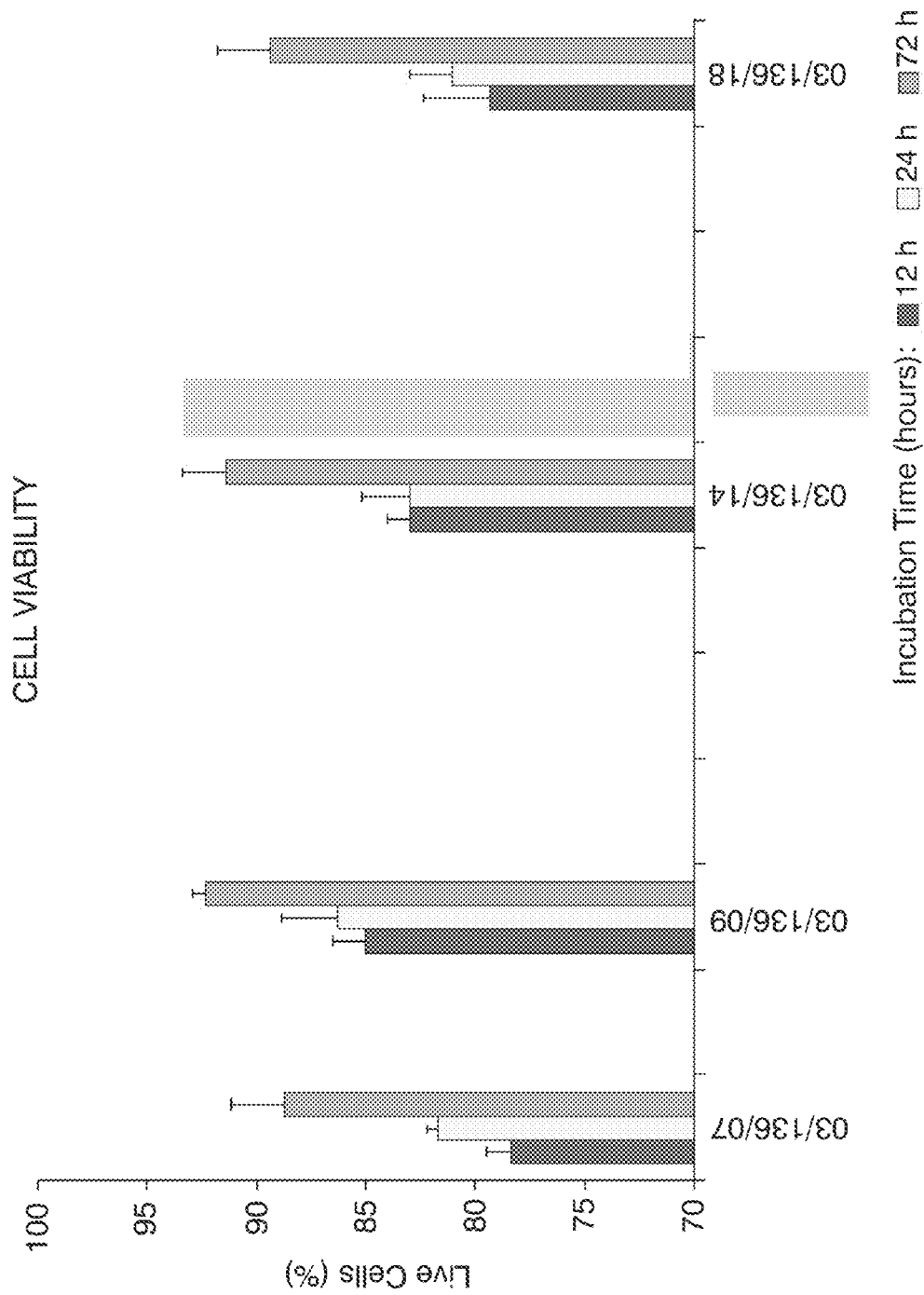
FIG. 5 shows the cell viability at 12, 24 and 72 hours as an indicator of the cytotoxicity of the surface obtained by the method of the invention (03/136/14) with respect to that of other conventional surfaces.
Figure 6:
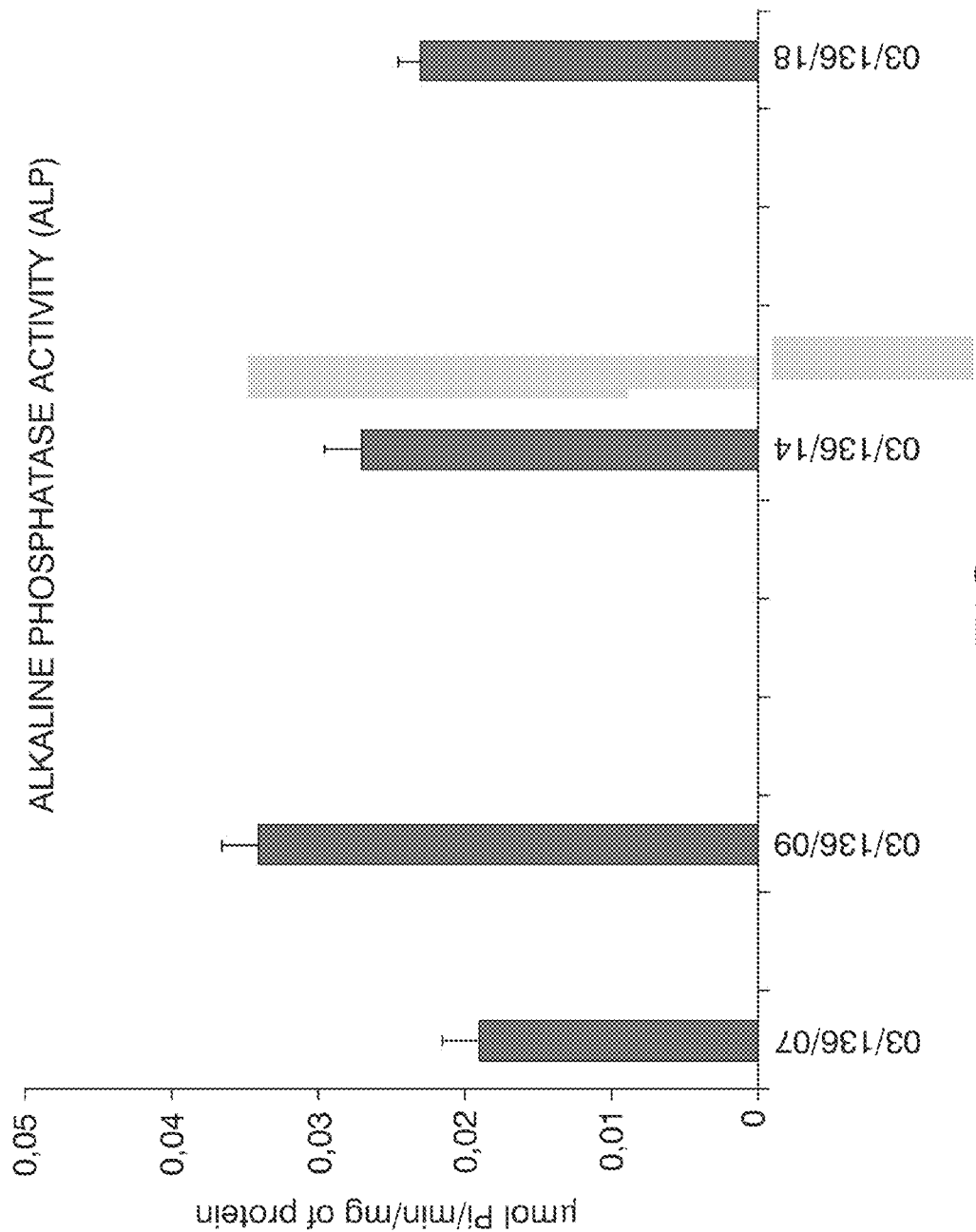
FIG. 6 shows the alkaline phosphatase activity after 6 days of culture as an indicator of bone matrix production by the osteoblasts seeded on the surface obtained by the method of the invention (03/136/14) with respect to that of other conventional surfaces.

FIG. 5 shows the results of the measurement of cell viability at 12, 24 and 72 hours in said samples. FIG. 6 in turn shows the results of the measurement of alkaline phosphatase activity after 6 days of culture of said samples.

Alkaline phosphatase activity has long been associated to biological calcification. Thus, the improved expression of this enzyme seems to be necessary before the mineralization of the bone matrix, providing the localized enrichment of inorganic phosphate for the nucleation and proliferation of hydroxylapatite crystals, the main component of bone tissue.

As can be seen in said FIGS. 5 and 6, the results obtained show a better cell response by the surface obtained by the method of the invention (code 03/136/14) with respect to the surface of the machining (code 03/136/07) and sandblasting (code 03/136/18) controls. On the other hand, the results of cell response of the surface of the invention are equivalent to those of the sandblasting and acid treatment control (code 03/136/09).

The invention claimed is:

1. A method for obtaining a treated surface of a titanium-based metal implant intended to be inserted into bone tissue, comprising:
    (a) projecting particles of aluminium oxide under pressure on an external area of the implant to form a sandblasted external area;
    (b) cleaning the sandblasted external area with a pressurized air, to provide a cleaned sandblasted external area;
    (c) chemically treating the cleaned sandblasted external area of the implant with an acid composition comprising sulfuric acid and hydrofluoric acid to form a sandblasted and chemically treated external area; and
    (d) thermally treating the sandblasted and chemically treated external area of the implant by heating at a temperature of 200-450° C. for 15-120 minutes to form a titanium oxide surface coating layer;
        wherein the acid treatment step, step (c) results in additional pitting of the cleaned, sandblasted external area.

2. The method according to claim 1, wherein the projection of the particles of aluminium oxide on the external area of step (a) is performed at a pressure of 1-6 atm.

3. The method according to claim 2, wherein the projection of the particles of aluminium oxide on the external area of step (a) is performed at a pressure of 3 atm.

4. The method according to claim 1, wherein the particles of aluminium oxide used in step (a) have a particle size of 10-100 µm.

5. The method according to claim 4, wherein the particles of aluminium oxide used in step (a) have a particle size of 25 µm.

6. The method according to claim 1, wherein the acid composition used in step (c) comprises 15-50% (v/v) sulfuric acid and 0.01-1% (v/v) hydrofluoric acid.

7. The method according to claim 6, wherein the acid composition used in step (c) comprises 28.8% (v/v) sulfuric acid and 0.024% (v/v) hydrofluoric acid.

8. The method according to claim 1, wherein the chemical treatment of step (c) is performed at a temperature of 50-110° C. for 4-60 minutes.

9. The method according to claim 8, wherein the chemical treatment of step (c) is performed at a temperature of 75° C. for 12 minutes.

10. The method according to claim 1, wherein the thermal treatment of step (d) is performed at a temperature of 285° C. for 60 minutes.

* * * * *